(12) United States Patent
Guadagno et al.

(10) Patent No.: US 9,372,197 B2
(45) Date of Patent: Jun. 21, 2016

(54) FLOURESCENT IN-SITU DETECTION OF LIPID PARTICLE APOLIPOPROTEINS WITHIN PRIMARY ELECTROPHORETIC MATRIX

(71) Applicant: Health Diagnostic Laboratory, Inc., Richmond, VA (US)

(72) Inventors: Philip Guadagno, Vashon Island, WA (US); Erin Grace Bellin, Sandston, VA (US)

(73) Assignee: True Health Diagnostics, LLC, Frisco, TX (US)

( * ) Notice: Subject to any disclaimer, the term of this patent is extended or adjusted under 35 U.S.C. 154(b) by 0 days.

(21) Appl. No.: 14/194,142

(22) Filed: Feb. 28, 2014

(65) Prior Publication Data

US 2014/0243431 A1    Aug. 28, 2014

Related U.S. Application Data

(60) Provisional application No. 61/770,406, filed on Feb. 28, 2013.

(51) Int. Cl.
| | |
|---|---|
| *G01N 33/53* | (2006.01) |
| *G01N 31/00* | (2006.01) |
| *G01N 33/92* | (2006.01) |
| *G01N 33/561* | (2006.01) |

(52) U.S. Cl.
CPC .............. *G01N 33/92* (2013.01); *G01N 33/561* (2013.01); *G01N 2550/00* (2013.01); *G01N 2800/32* (2013.01); *G01N 2800/50* (2013.01)

(58) Field of Classification Search
CPC ............... A61K 45/06; A61K 2300/00; C12N 2310/321
See application file for complete search history.

(56) References Cited

U.S. PATENT DOCUMENTS

| | | | |
|---|---|---|---|
| 9,005,419 B2 * | 4/2015 | Guadagno | G01N 27/44704 204/606 |
| 2012/0052594 A1 | 3/2012 | Guadagno | |

FOREIGN PATENT DOCUMENTS

| | | |
|---|---|---|
| WO | WO 2005059551 A2 | 6/2005 |
| WO | WO 2005066373 A1 | 7/2005 |
| WO | WO 2011091065 A2 | 7/2011 |
| WO | WO 2012071428 A2 | 5/2012 |
| WO | WO 2013181267 A1 | 12/2013 |

OTHER PUBLICATIONS

Vezina et al. Journal of Lipid Research, Vo.29, 1988, pp. 573-585.*
N. E. Walldius et al., "Apolipoprotein B and apolipoprotein A-I: risk indicators of coronary heart disease and targets for lipid-modifying therapy", J Int Med, vol. 255, Feb. 1, 2004 pp. 188-205.
Yusuf et al., "Effect of Potentially modifiable risk factors associated with myocardial infarction in 52 countries ( the Interheart study): case-control study", The Lancet, Lancet Limited. London, GB, vol. 364, No. 9438, Sep. 11, 2004, pp. 937-952.

* cited by examiner

*Primary Examiner* — Lisa Cook
(74) *Attorney, Agent, or Firm* — Perkins Coie LLP

(57) ABSTRACT

The present invention relates to, among other things, a gel electrophoresis system for detecting the level of specific Apolipoproteins and/or lipoprotein particles present in intact lipid particles in a biological sample. The system includes a gel substrate to receive a biological sample, at least two lipoprotein-binding complexes. Each complex includes an antibody that binds a lipoprotein particle or a portion thereof, which is bound to a signal producing molecule capable of producing or causing production of a detectable signal. The system also includes a device for detecting the detectable signal. The present invention also relates to methods of assessing the level of specific Apolipoproteins and/or lipoprotein particles present in a biological sample, determining whether a subject is at increased risk for cardiovascular disease, and monitoring the risk for developing cardiovascular disease.

12 Claims, 9 Drawing Sheets
(9 of 9 Drawing Sheet(s) Filed in Color)

Probes and samples were positioned as indicated in the image* below. The Tri-Valent probe is a combination of X-ApoB, X-ApoCIII and X-apoE. Antibody concentrations constant. *Fluorescence image generated on BioRad ChemiDoc MP.

Hi IDL sample 2

A  R-5, L-1 X-apoB

B  R-5, L-2 X-apoCIII

C  R-5, L-4 X-apoE

FIG. 10

FLOURESCENT IN-SITU DETECTION OF LIPID PARTICLE APOLIPOPROTEINS WITHIN PRIMARY ELECTROPHORETIC MATRIX

This application claims benefit of U.S. Provisional Patent Application Ser. No. 61/770,406, filed Feb. 28, 2013, which is hereby incorporated by reference in its entirety.

FIELD OF THE INVENTION

The present invention relates to the field of gel electrophoresis, and particularly in situ detection of lipid particles within an electrophoretic matrix.

BACKGROUND OF THE INVENTION

Electrophoresis is a technique used to separate charged species on the basis of size, electric charge, and other physical properties. In electrophoresis, the charged species migrate through a conductive electrophoretic medium, which may be (but is not required to be) a gel, under the influence of an electric field. Activated electrodes located at either end of the electrophoretic medium provide the driving force for the migration. The properties of the molecules, including their charge and mass, determine how rapidly the electric field causes them to migrate through the electrophoretic medium.

Many important biological molecules, such as amino acids, peptides, proteins, nucleotides, and nucleic acids, possess ionizable groups. Because of these ionizable groups, at any given pH, many important biological molecules exist in solution as electrically charged species. The electrically charged species enable doctors and scientists to separate nucleic acids and proteins using electrophoresis.

Separation of molecules, biological or otherwise, using electrophoresis depends on various forces, including charge and mass. When a biological sample, such as a protein or DNA, is mixed in a buffer solution and applied to an electrophoretic medium, these two forces act together. Separation using electrophoresis is possible because the rate of molecular migration through the electric field depends on the strength of the field, the charge, size, and shape of the molecules, and the ionic strength and temperature of the buffer through which the molecules are moving. During electrophoresis, the applied electrical field causes the molecules to move through the pores of the electrophoretic medium based on the molecular charge. The electrical potential at one electrode repels the molecules while the potential at the other electrode simultaneously attracts the molecules. The frictional force of the electrophoretic medium also aids in separating the molecules by size. Typically, after the applied electrical field has been removed, the molecules may be stained. After staining, the separated macromolecules can be seen in a series of bands spread from one end of the electrophoretic medium to the other. If these bands are sufficiently distinct, the molecules in these zones can be examined and studied separately by fixing macromolecules and washing the electrophoretic medium to remove the buffer solution.

Separating lipoprotein particles in bodily fluids (e.g., serum or plasma) provides information on the levels of various lipoprotein particles. Various disease states are linked to levels of apolipoproteins and/or lipoprotein particles including but not limited to cardiovascular disease, Alzheimer's disease, hyperlipidemia, abetalipoproteinemia, hypothyroidism, liver disease, diabetes mellitus, and renal problems. Higher levels of apolipoprotein B and LDL particles have been associated with increased risk of cardiovascular disease. It has been disclosed that differences in the amount of cholesterol in a particle may also play a role in the risk of cardiovascular disease. Small dense LDL, having more cholesterol ester, appears to be correlated with a higher risk of cardiovascular disease. However, increased levels of HDL correlate with a decrease in risk for cardiovascular disease. Thus, accurate predictors of the risk of an individual of developing various diseases related to lipoprotein particles are needed for research, diagnostic, and therapeutic purposes.

Current electrophoretic technologies for detection of apolipoproteins and lipoprotein particles cannot identify or discriminate the presence of apolipoproteins on multiple particles simultaneously. There is thus a need for a more efficient method of detecting apolipoproteins and lipoprotein particles in an electrophoretic matrix.

Existing strategies to measure, detect, and quantify lipid protein particles use non-specific protein dye to detect the fixed proteins in a gel, limiting specificity in the presence of coincident apolipoproteins on the fixed lipid particle and the variety of diagnostic measurements possible.

There is a need for an "in-situ" detection system which can affect all analytic operations efficiently within the single zonal electrophoretic matrix. All other electrophoresis associated systems require operations including but not limited to extra-gel sample preparation, pre-electrophoresis protein/apolipoprotein reduction and/or denaturation, off-gel or secondary gel post electrophoresis operations. A system and method that combines or avoids such steps has significant economic benefits.

This invention is directed to overcoming these and other deficiencies in the art.

SUMMARY OF THE INVENTION

One aspect of the invention relates to a gel electrophoresis system for detecting the level of specific Apolipoproteins and/or lipoprotein particles present in a biological sample. The system includes a gel substrate to receive a biological sample and at least two lipoprotein-binding complexes. Each complex includes an antibody that binds a lipoprotein particle or a portion thereof, where the antibody is bound to a signal producing molecule capable of producing or causing production of a detectable signal. Each detectable signal of the at least two lipoprotein-binding complexes is distinguishable from the other detectable signal. The system also includes a device for detecting the detectable signal, where the detecting indicates the level of the specific Apolipoproteins and/or lipoprotein particles in the biological sample.

Another aspect of the invention relates to a method of assessing the level of specific Apolipoproteins and/or lipoprotein particles present in a biological sample. This method includes the steps of providing a biological sample containing lipoprotein particles and providing at least two lipoprotein-binding complexes. Each complex includes an antibody that binds a lipoprotein particle or a portion thereof, where the antibody is bound to a signal producing molecule capable of producing or causing production of a detectable signal. Each detectable signal of the at least two lipoprotein-binding complexes is distinguishable from the other detectable signal. This method also includes contacting the biological sample with the antibody under conditions suitable to form a lipoprotein-antibody-signal producing molecule complex and separating the lipoprotein particles present in the biological sample by depositing the biological sample on an electrophoretic gel and carrying out gel electrophoresis. This method further includes detecting the detectable signal produced by the signal producing molecule of the lipoproteinantibody-signal producing molecule complex on the electrophoretic gel and determining the level of the specific Apolipoprotein and/or lipoprotein particle present in the biological sample based on the detecting.

A further aspect of the invention relates to a method of determining whether a subject is at increased risk for cardiovascular disease. This method includes assessing the level of specific Apolipoproteins and/or lipoprotein particles present in a biological sample. The assessing includes the steps of providing a biological sample containing lipoprotein particles and providing at least two lipoprotein-binding complexes. Each complex includes an antibody that binds a lipoprotein particle or a portion thereof, where the antibody is bound to a signal producing molecule capable of producing or causing production of a detectable signal. Each detectable signal of the at least two lipoprotein-binding complexes is distinguishable from the other detectable signal. The assessing step also includes separating the lipid protein particles present in the biological sample by depositing the biological sample on an electrophoretic gel and carrying out gel electrophoresis; contacting the biological sample with the at least two lipoprotein-binding complexes under conditions suitable to form a lipoprotein-antibody-signal producing molecule complex; detecting the detectable signal produced by the signal producing molecule of the lipoprotein-antibody-signal producing molecule complex on the electrophoretic gel; and determining the level of the specific Apolipoprotein and/or lipoprotein particle present in the biological sample based on the detecting. The method also includes the step of correlating the determined level of the Apolipoprotein and/or lipoprotein particle to a control or reference value to determine if the subject is at an increased risk for cardiovascular disease.

Prior electrophoretic technology required transfer protocols or traditional IFE non-protein specific staining of crosslinked probed complex. Further, existing strategies to measure detect and quantify lipid protein particles use non-specific protein dye to detect the fixed proteins in a gel (U.S. Patent Application Publication No. 2012/0052594, which is hereby incorporated by reference in its entirety), limiting specificity in the presence of coincident apolipoproteins on the fixed lipid particle and the variety of diagnostic measurements possible. This invention provides more efficient systems and methods to detect and quantify apolipoproteins and lipoproteins particles that avoid the use of transfer-blot technology.

To carry out the invention, fluorescent tagged primary and/or secondary antibodies may be used in concert with conventional lipoprotein electrophoresis techniques and instrumentation. Fluorescent antibody tags in solution can come in physical contact with the sample before the sample is applied to the gel, immediately after sample application, during electrophoresis as antibodies can be contained within the gel matrix, or post electrophoresis. The primary gel may then be washed, blotted, and dried, and the signal evaluated on the gel to which the sample was applied (i.e., in situ detection).

This type of integration of fluorescent antibodies with conventional single gel electrophoresis is unique. Electrophoresis measures lipid particle composition, (core lipids, membrane lipids, and apolipoproteins), simultaneously on all lipid particles. Direct methods can only target a specific component on a specific particle with additional non-reversible particle separation techniques. That is, to obtain intra particle composition, direct methods must first separate certain particles then probe remaining particles for component of interest. Often, the separation techniques are a particle compromise and limit quantitative analysis in particular. Dynamic inter-particle or intra-particle composition is not possible with direct methods since such methods measure specific targets after exclusion (e.g., precipitation, surfactant blockage, etc.) directly. Former fluorescent antibody-protein tags used with direct methods could not identify or discriminate the presence of apolipoproteins on multiple particles simultaneously. Thus, the invention provides significant advantages over prior technology. A significant advantage relates to multiple antibodies that may be cocktailed, each coupled to different reporters, to probe the same electrophoresed sample (e.g., in a single electrophoretic lane) for multiple apolipoproteins and/or lipoprotein particles. Such in situ detection is unprecedented in zonal gel electrophoresis providing, among other advantages, significant time, labor, and cost savings.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 3C (bottom left) is a raw image of the Alexa 647 emission and FIG. 3B (upper right) is a raw image of the Alexa 488 emission taken from the same gel at different wavelengths. FIG. 3A (upper left image) is processed for the user to visualize the combination images in different colors.

FIG. 4C (bottom left) is a raw image of the Alexa 488 and Alexa 546 emissions, FIG. 4D) is a raw image of the Alexa 647 emissions, and FIG. 4B (upper right) is a raw image of the Alexa 488 emission taken from the same gel at different wavelengths. FIG. 4A (upper left image) is processed for the user to visualize the trivalent combination images in different colors.

FIG. 5A shows results for row 1, column 1 (anti-ApoB) of the gel of FIGS. 4A-4C, showing dominant peaks near LDL and VLDL positions. FIG. 5B shows results for row 1, lane 2 (anti-ApoCIII), showing a dominant peaks near the VLDL position. FIG. 5C shows results for anti-ApoE, showing a dominant peak near the VLDL position.

FIG. 6A shows results for row 2, column 1 (anti-ApoB) of the gel figure, showing dominant peak near the VLDL position. FIG. 6B shows results for row 2, lane 2 (anti-ApoCIII), showing a dominant peak near the VLDL position. FIG. 6C shows results for anti-ApoE, showing a dominant peak near the VLDL position.

FIG. 7A is row 3, column 1 (anti-ApoB) of the gel, showing dominant peak near the IDL position. FIG. 7B shows results for row 3, lane 2 (anti-ApoCIII) of the gel, showing a dominant peak near the VLDL position. FIG. 7C shows results for anti-ApoE showing a dominant peak near the VLDL position.

FIG. 8A shows results for row 2, column 1 (anti-ApoB) of the gel figure, showing a dominant peak near the LDL position (no HDL would be detected with anto-ApoB). FIG. 8B shows results for row 4, lane 2 (anti-ApoCIII), showing dominant peaks near Lp(a) and HDL positions. FIG. 8C shows results for anti-ApoE, showing dominant peaks near the IDL and Lp(a) positions.

FIG. 7A shows results for row 3, column 1 (anti-ApoB) of the gel figure, showing a dominant IDL peak. FIG. 7B shows results for row 3, lane 2 (anti-ApoCIII) showing a dominant VLDL peak. FIG. 7C shows results for anti-ApoE showing a dominant VLDL peak.

Figure 10:
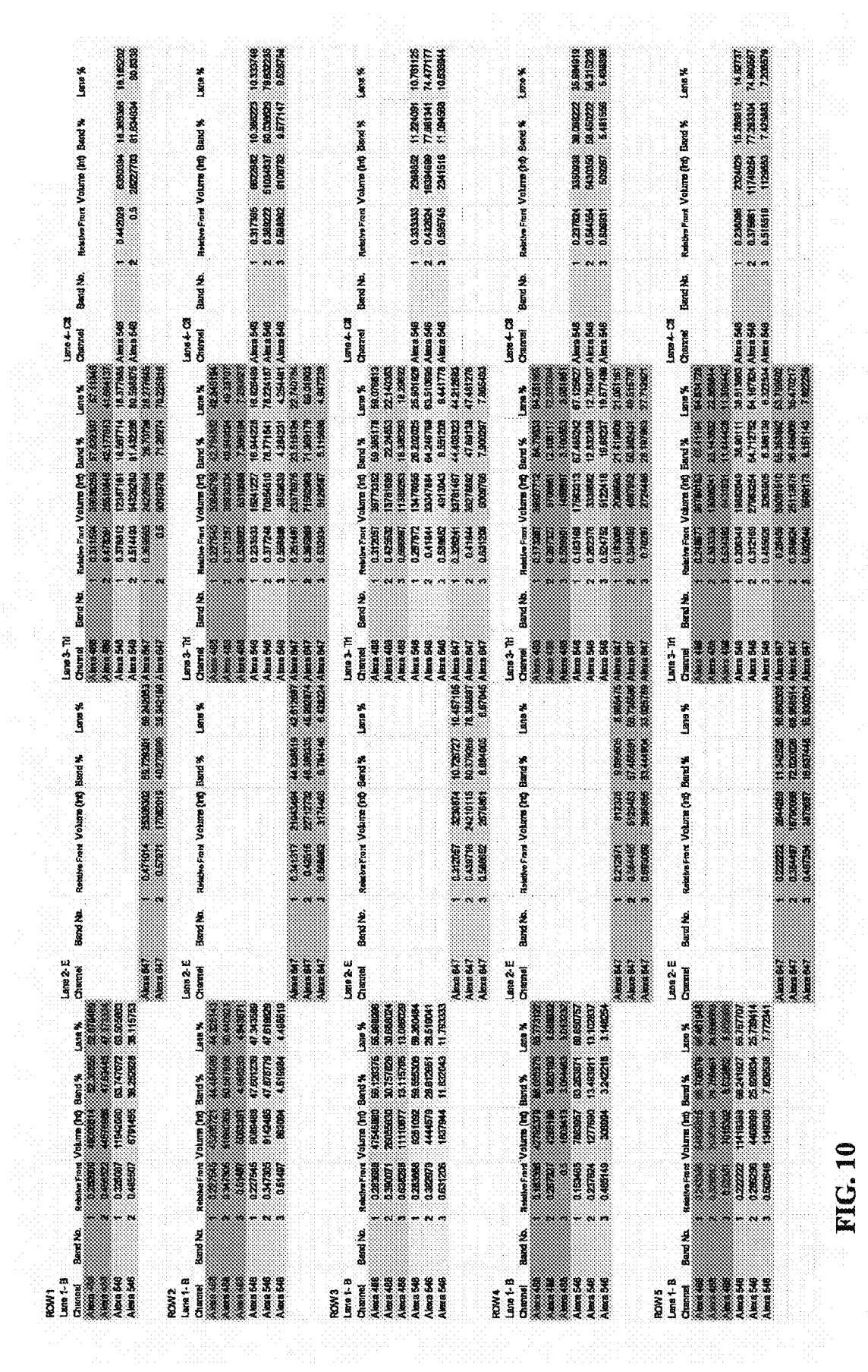

FIG. 10 contains the complete table of numeric density values by row, lane and dye type, corresponding to FIGS. 4 to 9.

DETAILED DESCRIPTION OF THE INVENTION

Figure 1:
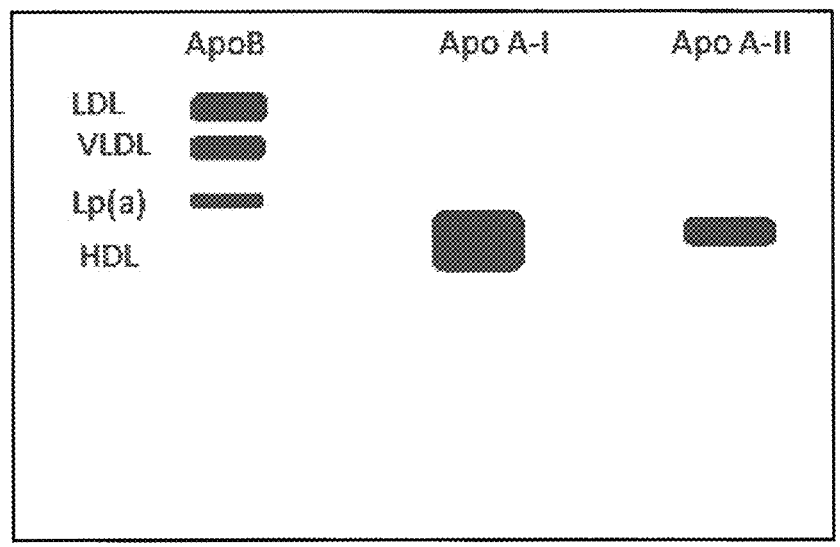
FIG. 1 is a schematic illustration of a gel after non-specific lipoprotein immunofixation electrophoresis ("Lipo-IFE").

One aspect of the invention relates to a gel electrophoresis system for detecting the level of specific Apolipoproteins and/or lipoprotein particles present in a biological sample. The system includes a gel substrate to receive a biological sample and at least two lipoprotein-binding complexes. Each complex includes an antibody that binds a lipoprotein particle or a portion thereof, where the antibody is bound to a signal producing molecule capable of producing or causing production of a detectable signal. Each detectable signal of the at least two lipoprotein-binding complexes is distinguishable from the other detectable signal. The system also includes a device for detecting the detectable signal, where the detecting indicates the level of the specific Apolipoproteins and/or lipoprotein particles in the biological sample.

The terms "lipoprotein particle," "lipid protein particle," "lipid particle," and the like as used herein refers to a particle that contains both protein and lipid. Examples of lipoprotein particles are described in more detail below.

The term "lipoprotein particle number" as used herein refers to the number of the lipoprotein particles present in the bodily fluid.

The term "apolipoprotein" as used herein refers to a protein that combines with lipids to form a lipoprotein particle. Examples of apolipoprotein types are described in more detail below. The unique nature of the apolipoprotein is their stoichiometric relationship to lipoprotein particles, providing an estimate of the lipoprotein particle number, which is described in more detail below.

Suitable biological samples or biosamples according to the invention include human biological matrices, urine, plasma, serum, and human lipoprotein fractions. For example, the sample may be fresh blood or stored blood or blood fractions. The sample may be a blood sample expressly obtained for the assays of this invention or a blood sample obtained for another purpose which can be subsampled for use in accordance with the methods according to the invention. For instance, the biological sample may be whole blood. Whole blood may be obtained from the subject using standard clinical procedures. The biological sample may also be plasma. Plasma may be obtained from whole blood samples by centrifugation of anti-coagulated blood. The biological sample may also be serum. The sample may be pretreated as necessary by dilution in an appropriate buffer solution, concentrated if desired, or fractionated by any number of methods including but not limited to ultracentrifugation, fractionation by fast performance liquid chromatography (FPLC), or precipitation. Any of a number of standard aqueous buffer solutions, employing one of a variety of buffers, such as phosphate, Tris, or the like, at physiological to alkaline pH can be used.

As background, fatty acids, cholesterol, monoacylglycerols, and bile acids are absorbed in the intestine. Bile acids are found in intestinal bile and aid in the digestion of fats by the formation of micelles to emulsify the fats. Bile acids are stored in the gallbladder until they are secreted into the intestine after eating. Intestinal epithelial cells synthesize triacylglycerols. A portion of the cholesterol is esterified to form cholesterol esters. Intestinal cells form chylomicrons from triacylglycerols, cholesterol esters, phospholipids, free cholesterol, and apolipoproteins.

Specific lipoprotein particles or portions thereof that may be detected according to the invention include, but are not limited to, Apolipoprotein A, Apolipoprotein B, Apolipoprotein C, Apolipoprotein D, Apolipoprotein E, Apolipoprotein H, lipoprotein (a), high density lipoprotein, intermediate density lipoprotein, low density lipoprotein, very low density lipoprotein, Chylomicrons, Lipoprotein X, oxidized variants or mixtures thereof.

Apolipoproteins are the protein component of lipoprotein particles. Apolipoproteins coat lipoprotein particles that include cholesterol esters and triacylglyceride. The coat of the lipoprotein particle is made up of unesterified cholesterol, phospholipids, and apolipoproteins. The unique nature of the apolipoprotein is their stoichiometric relationship to lipoprotein particles, providing an estimate of the lipoprotein particle number. These lipoprotein particles provide a way to circulate the hydrophobic components throughout the bloodstream. Different lipoprotein particles include chylomicron-P, VLDL-P, IDL-P, LDL-P, Lp(a)-P and HDL-P. Lipoprotein particles vary in size, shape, density, apolipoprotein composition, and lipid composition. There is heterogeneity within each class with each class sharing similar physical characteristics. By varying conditions, it is possible to visualize different particles within a class. There is clinical merit in doing so because, for example, one class may be artherogenic and one class may be artheroprotective.

The apolipoprotein A (Apo A) family constitute the major proteins found in HDL-P and triglyceride-rich lipoprotein particles. Apo A, as part of HDL, is involved in the removal of free cholesterol from extrahepatic tissues and also plays a role in the activation of lecithin acyltransferase. Apolipoprotein A activates the enzymes driving cholesterol transfer from the tissues into HDL and is also involved in HDL recognition and receptors binding in the liver.

There are multiple forms of apolipoprotein A. The most common forms are Apo A-I and Apo A-II. Apolipoprotein A (A-I, A-II, and A-IV) are found in chylomicrons and HDL. Apo A-I is the major apolipoprotein A attached to HDL. Apo A-I is responsible for activating lecithin-cholesterol acyltransferase and Apo A-II modulates that activation. Lecithin-cholesterol acyltransferase converts free cholesterol into a cholesterol ester. Apo A-IV secretions increase when fat is absorbed in the intestines. Apo A-IV may also function in activation of lecithin-cholesterol acyltransferase.

Apo A-I is found in greater proportion than Apo A-II (about 3 to 1). Lower levels of Apo A commonly correlate with the presence of cardiovascular disease (CVD) and peripheral vascular disease. Apo A-I may be a better predictor of atherogenic risk than HDL-cholesterol (HDL-C). Certain genetic disorders cause Apo A-I deficiencies and associated low levels of HDL particles. These patients also tend to have hyperlipidemia with elevated LDL particles. This contributes to accelerated rates of atherosclerosis. Apo A levels may be extremely low in alpha lipoproteinemia (also known as familial high density lipoprotein deficiency).

The role of HDL and its major apolipoprotein Apo A-I in cholesterol efflux from macrophages has been studied extensively. While HDL competes for Apo A-I binding, Apo A-I is not a competitor for HDL binding. This observation suggests that HDL and Apo A-I are binding to macrophages at least in part by distinct receptors. For example, pre-β-HDL and lipid-free Apo A-I are poor ligands for the scavenger receptor (SR-BI), explaining the lack of competition of HDL binding by Apo A-I. Conversely, it has been shown that Apo A-I can dissociate from HDL, so that lipid-free Apo A-I could be available for the competition of the Apo A-I binding site by HDL. Lorenzi et al., "Apolipoprotein A-I but not high-density lipoproteins are internalised by RAW macrophages: roles of ATP-binding cassette transporter A1 and scavenger receptor." *BIJ Mol Med.* 86:171-183 (2008), which is hereby incorporated by reference in its entirety. Apo A-II, another component of HDL, has been shown to be pro-atherogenic in animal models. Meyers et al., "Pharmacologic elevation of high-density lipoproteins: recent insights on mechanism of action and atherosclerosis protection." *Curr Opin Cardiol.* 19(4): 366-373 (2004), which is hereby incorporated by reference in its entirety.

Apolipoprotein B (Apo B-100 and Apo B-48) is the protein component of LDL. One molecule of Apo B is present in the phospholipid layer of each LDL. Over 90% of the LDL particle is composed of Apo B. Apo B functions to solubilize cholesterol within the LDL complex, which in turn increases the transport capacity of LDL for subsequent deposit of LDL cholesterol on the arterial wall. The deposit contributes to cardiovascular disease. Apo B is also a protein component of chylomicrons, VLDL, IDL, and Lp(a). Apo B is a large amphipathic helical glycoprotein with 2 isoforms: Apo B-100 (synthesized in the hepatocytes) and Apo B-48 (the structural protein of chylomicrons). Chylomicrons contain Apo B-48 while other lipoprotein particles that contain Apo B contain Apo B-100.

Apo B modulates the activity of enzymes that act on lipoprotein particles, maintains the structural integrity of the lipoprotein particle complex, and facilitates the uptake of lipoprotein particles by acting as ligands for specific cell-surface receptors. Enzymes that act on lipoprotein particles include but are not limited to lipoprotein lipase, lecithin-cholesterol acyltransferease, hepatic-triglyceride lipase, and cholesterol ester transfer protein. Elevated levels of Apo B are found in hyperlipoproteinemia. Apo B-100 is absent in forms of abetalipoproteinemia. High levels of Apo B-100 may be present in hyperlipoproteinemia, acute angina, and myocardial infarction. Apo B-48 stays in the intestine in chylomicron retention disease.

It is well established that increased plasma concentration of Apo B-containing lipoprotein particles is associated with an increased risk of developing atherosclerotic disease. Case control studies have found plasma Apo B concentrations to be more discriminating than other plasma lipids and lipoprotein particles in identifying patients with coronary heart disease (CHD). See De Backer et al., "European Guidelines on Cardiovascular Disease Prevention in Clinical Practice. Third Joint Task Force of European and other Societies on Cardiovascular Disease Prevention in Clinical Practice," *Eur Heart J* 24:1601-1610 (2003); Walldius & Jungner, "Apolipoprotein B and Apolipoprotein A-I: Risk Indicators of Coronary Heart Disease and Targets for Lipid-modifying Therapy," *J Intern Med* 255(2): 188-205 (2004); Walldius, et al., "The apoB/apoA-I ratio: A Strong, New Risk Factor for Cardiovascular Disease and a Target for Lipid-Lowering Therapy—A Review of the Evidence," *J Intern Med.* 259(5): 493-519 (2006); Yusuf et al., "Effect of Potentially Modifiable Risk Factors Associated with Myocardial Infarction in 52 Countries (the INTERHEART Study): Case-control Study," *Lancet* 364: 937-52 (2004), which are hereby incorporated by reference in their entirety). The utility of Apo B in determining CHD risk has been confirmed by prospective studies, although the extent to which Apo B concentrations were better than serum lipids in predicting risk was variable. Apo B is a component of all atherogenic or potentially atherogenic particles, including very low density lipoprotein particles (VLDL-P), intermediate density lipoprotein particles (IDL-P), low density lipoprotein particles (LDL-P), and lipoprotein(a) particles (Lp(a)-P), and each particle contains one molecule of Apo B. Therefore, Apo B provides a direct measure of the number of atherogenic lipoprotein particles in the circulation. Total Apo B is not homogeneous. Total Apo B will be influenced by its presence of Apo B in the various particles above. Measuring total Apo B alone without separating the particles does not indicate with which particle it is associated.

There is now a clear consensus that Apo B is more strongly predictive of cardiovascular disease (CVD) than low density lipoprotein cholesterol (LDL-C) and a recent consensus conference report from the American Diabetes Association (ADA) and the American College of Cardiology (ACC) recognizes the importance of measurement of Apo B (see Kannel et al., "Cholesterol in the Prediction of Atherosclerotic Disease," *Ann Intern Med* 90:85-91 (1979) and Jeyarajah et al., "Lipoprotein Particle Analysis by Nuclear Magnetic Resonance Spectroscopy," Clin Lab Med 26: 847-70 (2006), which are hereby incorporated by reference in their entirety). An elevated level of Apo B and LDL-P signifies that an individual has increased risk for cardiovascular disease. An elevated level of Apo B and Lp(a)-P signifies that an individual has increased risk for cardiovascular disease.

Further, the Apo B/Apo A-I ratio has been shown to be strongly related to risk of myocardial infarction (MI), stroke and other CV manifestations as shown in the Apolipoprotein-related mortality risk (AMORIS) (See Walldius & Jungner, "Apolipoprotein B and Apolipoprotein A-I: Risk Indicators of Coronary Heart Disease and Targets for Lipid-modifying Therapy," *J Intern Med* 255(2): 188-205 (2004); Walldius, et al., "The apoB/apoA-I ratio: A Strong, New Risk Factor for Cardiovascular Disease and a Target for Lipid-Lowering Therapy—A Review of the Evidence," *J Intern Med.* 259(5): 493-519 (2006); Walldius et al., "Stroke Mortality and the Apo B/Apo A-I Ratio: Results of the AMORIS Prospective Study." *J Intern Med.* 259: 259-66 (2006), which are hereby incorporated by reference in their entirety) and INTER-HEART (Yusuf et al., "Effect of Potentially Modifiable Risk Factors Associated with Myocardial Infarction in 52 Countries (the INTERHEART Study): Case-control Study," *Lancet* 364: 937-52 (2004) and Yusuf et al., "Obesity and the risk of myocardial infarction in 27,000 participants from 52 countries: a case-control study," *Lancet* 366: 1640-9 (2005), which are hereby incorporated by reference in their entirety) studies.

Apolipoprotein C (Apo C-I, C-II, C-III) is a component of chylomicron particles, VLDL particles, IDL particles, and HDL particles. Apo C-II is an activator of lipoprotein lipase and a deficiency results in an accumulation of chylomicrons and triacylglycerols. High levels of Apo C-II are indicators of angina and myocardial infarction. Apolipoprotein C-II (Apo C-II) is a specific type of protein found in large particles absorbed from the gastrointestinal tract. It is also found in very low density lipoprotein particles (VLDL-P) which is made up of mostly cholesterol. Apo C-II is an apolipoprotein responsible for the activation of lipoprotein lipase (LPL) in capillaries and thus begins the catabolism of the chylomicron particles and VLDL-P. It is also found in HDL-P. Deficits of this Apo C-II present with grave hypertriglyceridemia and hyperchylomicronemia during fasting.

Apo C-II measurements can help to determine the specific type or cause of high blood lipids (hyperlipidemia). Persons with familial lipoprotein lipase deficiency may have high amounts of Apo C-II. Other disorders that may be associated with high Apo C-II levels include angina pectoris and heart attack. Low Apo C-II levels are seen in persons with a rare condition called familial Apo C-II deficiency.

Apolipoprotein C-III (Apo C-III) is found in very low density lipoprotein particles (VLDL-P). Apolipoprotein C-III is a small protein also found on LDL, chylomicron, and HDL particles. Apo C-III inhibits lipoprotein lipase and hepatic lipase and it is thought to inhibit hepatic uptake and delay catabolism of triglyceride-rich particles. An increase in Apo C-III levels contributes to the development of hypertriglyceridemia.

Apo C-IV is found in at least VLDL-P and HDL-P.

The Apo A-I, Apo C-III and Apo A-IV genes are closely linked in both rat and human genomes. The A-I and A-IV genes are transcribed from the same strand, while the A-I and C-III genes are convergently transcribed. An increase in Apo C-III levels induces the development of hypertriglyceridemia.

Apolipoprotein D is a minor component of HDL. High concentrations of Apo D are correlated with various diseases such as gross cystic disease of the breast and Alzheimer's disease.

Apolipoprotein E (Apo E-2, E-3, and E-4) are found in chylomicrons and IDL. Apo E binds to a receptor on liver cells and peripheral cells. Apo E is essential for the normal catabolism of triglyceride-rich lipoprotein particle constituents. Apo E was initially recognized for its importance in lipoprotein particle metabolism and cardiovascular disease. It plays a role in the transport of lipids to the tissues, the transport of cholesterol from the organs to the liver, in lipoprotein particle metabolism by clearing VLDL and chylomicrons, and in formation of atherosclerotic lesions. The Apo E portion of the lipoprotein particles mediates the binding of Apo E lipoprotein particles to the LDL receptor. Apo E bound to HDL-P inhibits agonist induced platelet aggregation by binding to sites on the platelets. Three different alleles of the Apo E gene exist, Apo E e2, e3, and e4. Apo E e4 is associated with an increased risk of late onset Alzheimer's disease.

Apolipoprotein H functions to bind cardiolipin. Anti-cardiolipin antibodies are found in syphilis, sclerosis, and lupus and in some diseases the antibodies require Apo H to be active and inhibit serotonin release by the platelets and prevent aggregation of platelets. Apo H also inhibits serotonin release by platelets and prevents aggregation of platelets.

Lipoprotein particle profiles are different for different individuals and for the same individual at different times. Chylomicrons are produced in the intestine and transport digested fat to the tissues. Lipoprotein lipase hydrolyzes triacylgylcerol to form fatty acids. Chylomicrons are one of the largest buoyant particles. VLDL is formed from free fatty acids upon metabolism of chylomicrons in the liver. Lipoprotein lipase hydrolyzes triacylgylcerol to form fatty acids. IDL is the unhydrolyzed triacylglycerol of VLDL. IDL becomes LDL due to hepatic lipase. HDL plays a role in the transfer of cholesterol to the liver from peripheral tissues. HDL is synthesized in the liver and intestines.

LDL particles bind to LDL receptors. Upon receptor binding, LDL is removed from the blood. Cells use cholesterol within the LDL for membranes and hormone synthesis. LDL deposits LDL cholesterol on the arterial wall which contributes to cardiovascular disease. LDL causes inflammation when it builds up inside an artery wall. Macrophages are attracted to the inflammation and turn into foam cells when they take up LDL, causing further inflammation. Smaller, denser LDL contain more cholesterol ester than the larger, buoyant LDL.

The structure of the lipoprotein(a) particles (LP(a)-P) is that of an LDL-like particle with lipoprotein(a) bound to apolipoprotein B by a disulfide bond. Lipoprotein(a) particles appear to play a role in coagulation and may stimulate immune cells to deposit cholesterol on arterial walls. A high lipoprotein(a)-P level indicates a higher risk for cardiovascular disease. Therefore, Lp(a)-P is useful in diagnostic and statistical risk assessment. Lp(a)-P may serve to facilitate LDL-P plaque deposition. Levels of Lp(a)-P are increased in atherogenic events.

Lp(a)-P may have a link between thrombosis and atherosclerosis, interfering with plasminogen function in the fibrinolytic cascade. Numerous studies have documented the relationship of high plasma Lp(a)-P concentrations to a variety of cardiovascular disorders, including peripheral vascular disease, cerebrovascular disease, and premature coronary disease. One large study of older Americans, in particular, demonstrated elevated levels of Lp(a)-P independently predict an increased risk of stroke, death from vascular disease, and death from all causes in men (see Fried et al., "The Cardiovascular Health Study: Design and Rationale," *Ann. Epidemiol.* 3:263-76 (1991), which is hereby incorporated by reference in its entirety).

Low-density lipoprotein cholesterol, (LDL-C), has been used for measurement for assessing cardiovascular risk. However, due to the variability of LDL-C, Apo B is a better measure of circulating LDL particle number (LDL-P) and therefore a more reliable indicator of risk than that traditional LDL-C because there is 1:1 stoichiometry of Apo B and LDL particles. The sum of total Apo B includes but is not limited to the Apo B complement of LDL-P (large buoyant particles and small dense particles), +VLDL+IDL+Lp(a)+chylomicrons. Measurement of Apo B levels and associated lipoprotein particles provides additional information on the risk of atherosclerotic heart disease beyond that of the individual measurements or the traditional LDL-C assays. Measurement of fasting plasma insulin levels and LDL particle size also provide useful information.

Oxidized variants of the above-noted lipoproteins may also be detected. Oxidized variants of lipoproteins contribute to atherogenesis, with oxidation leading to increased intracellular calcium, lowered energy production, activation of cytokines, membrane damage, all resulting in apoptosis, necrosis, and ultimately cell death. Oxidation typically begins when a reactive radical abstracts a hydrogen atom from a polyunsaturated fatty acid on the LDL particle. Lipid peroxyl and alkoxyl radicals are formed, which in turn can initiate oxidation in neighboring fatty acids, resulting in propogation of lipid peroxidation. These oxidized forms of lipoproteins are absorbed by macrophages more rapidly than the native lipoproteins and this results in macrophage cholesterol accumulation, and subsequent foam cell formation and inhibition of the motility of tissue macrophages and endothelial cells. This cascade of events results in vascular dysfunction and formation and activation of atherosclerotic lesions.

The gel electrophoresis may be one-dimensional or two-dimensional. Isoelectric focusing may also be performed.

Electrophoretic gel substrates suitable for use with the invention are known to those of skill in the art. For instance, suitable gel substrates include, but are not limited to, agarose or polyacrylamide. SDS-PAGE (polyacrylamide) gels separate proteins based on their size because the SDS coats the proteins with a negative charge. Separation of proteins on the agarose gel is by charge.

Electrophoretic gels of varying sizes may contain various numbers of lanes (e.g., one, two, three, four, five, six, seven, eight, nine, ten, etc.). The biological sample from a single individual or subject may be probed to identify multiple components and/or serum from multiple individuals may be tested. The protocols for conducting electrophoresis on different sizes of gels will be similar except that modifications may be made to optimize separation on that size of gel.

As noted above, each complex includes an antibody that binds a lipoprotein particle or a portion thereof, where the antibody is bound to a signal producing molecule capable of producing or causing production of a detectable signal.

As used herein, the term "antibody" is meant to include intact immunoglobulins derived from natural sources or from recombinant sources, as well as immunoreactive portions (i.e. antigen binding portions) of intact immunoglobulins. The antibodies of the invention may exist in a variety of forms including, for example, polyclonal antibodies, monoclonal antibodies, intracellular antibodies, antibody fragments (e.g. Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988), which are hereby incorporated by reference in their entirety).

Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Procedures for raising polyclonal antibodies are also well known (Ed Harlow and David Lane, USING ANTIBODIES: A LABORATORY MANUAL (Cold Spring Harbor Laboratory Press, 1988), which is hereby incorporated by reference in its entirety).

For example, polyclonal antibodies to an apolipoprotein may be produced by injecting a suitable animal host, such as a rabbit, with the apolipoprotein of interest and an adjuvant. Approximately 0.02 milliliters may be injected, with reinjection occurring every 21 days until peak antibody titer is achieved. Antibody titer may be tested by, for example, an ear bleed. Antibodies to Apo B-100 or other apolipoprotein may be produced in this manner. Alternatively, antibodies to Apo B-100 or other apolipoprotein may be purchased commercially.

Antibodies can be generated with high levels of specificity, sufficient to distinguish different isoforms of the same proteins, such as small Lp(a) and large Lp(a). Such antibodies would be labeled with, for example, different color fluorescent probes and the apolipoprotein type can be distinguished with extreme detail. As described below, absolute levels and ratios of detailed measurements can be reported and converted into a risk factor. For example the ratio of small to large Lp(a) can be reported with a specific cutoffs for high-, medium-, and low-risk ranges.

In addition to whole antibodies, the invention encompasses binding portions of such antibodies. Such binding portions include the monovalent Fab fragments, Fv fragments (e.g., single-chain antibody, scFv), single variable $V_H$ and $V_L$ domains, and the bivalent $F(ab')_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Suitable signal producing molecules that are capable of producing or causing production of a detectable signal will be known to those of skill in the art. The detectable signal includes any signal suitable for detection and/or measurement by radiometric, colorimetric, fluorometric, size-separation, or precipitation means, or other means known in the art.

Examples of signal producing molecules that are capable of producing or causing production of a detectable signal include various enzymes, prosthetic groups, fluorescent materials, luminescent materials, bioluminescent materials, radioactive materials, positron emitting metals, and nonradioactive paramagnetic metal ions. The signal producing molecules may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the invention. Further examples include, but not limited to, various enzymes. Examples of enzymes include, but are not limited to, horseradish peroxidase, alkaline phosphatase, beta-galactosidase, or acetylcholinesterase; prosthetic group complexes such as, but not limited to, streptavidin/biotin and avidin/biotin. Examples of fluorescent materials include, but are not limited to, umbelliferone, fluorescein, fluorescein isothiocyanate, rhodamine, dichlorotriazinylamine fluorescein, dansyl chloride or phycoerythrin. Examples of luminescent material include, but are not limited to, luminol. Examples of bioluminescent materials include, but not limited to, luciferase, luciferin, and aequorin. Examples of radioactive material include, but are not limited to, bismuth (213Bi), carbon (14C), chromium (51Cr), (153Gd, 159Gd)5 gallium (68Ga, 67Ga), germanium (68Ge), holmium (166Ho), indium (115In, 113In, 112In, 111In), iodine (131I, 125I, 123I, 121I), lanthanium (140La), lutetium (177Lu), manganese (54Mn), molybdenum (99Mo), palladium (103Pd), phosphorous (32P), praseodymium (142Pr), promethium (149Pm), rhenium (186Re, 188Re), rhodium (105Rh), ruthemium (97Ru), samarium (153Sm), scandium (47Sc), selenium (75Se), strontium (85Sr), sulfur ($^{35}$S), technetium (99Tc), thallium (201Ti), tin (113Sn, 117Sn), tritium (3H), xenon (133Xe), ytterbium (169Yb, 175Yb), yttrium (90Y), zinc (65Zn). Further examples include positron emitting metals using various positron emission tomographies, and nonradioactive paramagnetic metal ions.

Detection of an antibody-signal producing molecule complex in accordance with the invention may also be achieved by addition of a reagent capable of interacting with the signal producing molecule, where the signal producing molecule produces a detectable signal upon contact with the reagent. For example, light is emitted when luciferase acts on the appropriate luciferin substrate.

A secondary antibody that is coupled to a detectable signal or moiety, such as for example, an enzyme (e.g., luciferase), fluorophore, or chromophore may also be used.

As noted above, each detectable signal of the at least two lipoprotein-binding complexes is distinguishable from the other detectable signal. This permits cocktailing at least two lipoprotein-binding complexes where each of the complexes detects a different lipoprotein particle or a portion thereof, each complex also producing or capable of producing a different detectable signal. For example, a first lipoprotein-binding complex may include fluorescein isothiocyanate (FITC)-labeled anti-Apo A1 antibody and a second lipoprotein-binding complex may include rhodamine-labeled anti-Apo A2 antibody. The first and second complexes may be mixed or cocktailed together and/or with additional (e.g., third, fourth, fifth, sixth, etc) complexes including antibodies that may recognize different lipoprotein particles or a portions thereof bound to further distinguishable signal-producing molecules. This permits probing of multiple antigens in a single electrophoretic lane.

For example, the signal producing molecules may include fluorescent tags. Fluorescence tagging and the detection of natural fluorescence in molecules is a method of analytical chemistry and biology that is well known in the art. The instruments used to detect fluorescence may include the following components. A light source with a broad optical bandwidth such as a light bulb or a laser is used as the source of the stimulating light. An optical filter is used to select the light at the desired stimulation wavelength and beam it onto the sample. Optical filters are available at essentially any wavelength and are typically constructed by the deposition of layers of thin film at a fraction of the wavelength of the desired transmission wavelength. The light that exits the optical filter is then applied to the sample to stimulate the fluorescent molecule.

The molecule then emits light at its characteristic fluorescent wavelength. This light is collected by a suitable lens and is then passed through a second optical filter centered at the characteristic wavelength before being brought to a detection device such as a photomultiplier tube, a photoconductive cell, or a semiconductor optical detector. Therefore, only light at the desired characteristic wavelength is detected to determine the presence of the fluorescent molecule. Accordingly, the at least two lipoprotein-binding complexes may include fluorescent molecules that emit light at different, distinguishable fluorescent wavelengths.

Fluorescent tags may be multiplexed in a single area such that they are optically distinct. For example, 5 different fluorescent tags, red, green, blue, yellow, and orange may be applied to the same limited area and be independently detected and distinguished by optical detection software. For example, the Life Technologies Alexa Fluor product line includes at least 19 distinct dyes that may be combined for tagging distinct antibodies to label and identify individual antigens. For example, as shown in the Examples described herein, Alexa 647, Alexa 546 and Alexa 488 may be combined for tagging distinct antibodies to label and identify individual antigens (e.g., Apo B, Apo C-III, and Apo E). Additional fluorophores such as Alexa 430 may be included to optimize a method and avoid cross-talk between labels. An optical system can quantitate the fluorescent signals and automatically normalize the signal value to generate relative densities or particle numbers. For example, by normalizing the extinction/emission coefficients or quantum relativity of each dye, relative values for concentration or particle number can be determined.

The system and methods may also include a device or use of a device for detecting the detectable signal, where the detecting indicates the level of the specific Apolipoproteins and/or lipoprotein particles in the biological sample. The device may also quantitate the level of specific Apolipoproteins and/or lipoprotein particles based on the detection of the signal producing molecule.

The presence of the lipoprotein particle or a portion thereof in the electrophoretic gel may then be quantified by measurement of the detectable signal or moiety. The particle number may then be calculated according to known stoichiometric relationships (e.g., 1:1 stoichiometry of Apo B and LDL particles). The particle number may be quantified by comparison with a separate analysis that characterizes the total lipid particle or class of lipid particle concentration in the sample. Such separate analysis may be ultracentrifugation, NMR, or any other analysis method that can characterize a concentration or total particle number for particles in the sample. Said sample used in lipid particle electrophoresis and lipid particle quantification may be different aliquots of the same sample.

Accordingly, another aspect of the invention relates to a method of assessing the level of specific Apolipoproteins and/or lipoprotein particles present in a biological sample. This method includes the steps of providing a biological sample comprising lipoprotein particles and providing at least two lipoprotein-binding complexes. Each complex includes an antibody that binds a lipoprotein particle or a portion thereof, where the antibody is bound to a signal producing molecule capable of producing or causing production of a detectable signal. Each detectable signal of the at least two lipoprotein-binding complexes is distinguishable from the other detectable signal. This method also includes contacting the biological sample with the antibody under conditions suitable to form a lipoprotein-antibody-signal producing molecule complex and separating the lipoprotein particles present in the biological sample by depositing the biological sample on an electrophoretic gel and carrying out gel electrophoresis and contacting the biological sample with the antibody under conditions suitable to form a lipoprotein-antibody-signal producing molecule complex. The antibody will both label the lipoprotein and fix the lipoprotein in place in the gel, preventing additional migration during subsequent wash steps. This method further includes detecting the detectable signal produced by the signal producing molecule of the lipoprotein-antibody-signal producing molecule complex on the electrophoretic gel and determining the level of the specific Apolipoprotein and/or lipoprotein particle present in the biological sample based on the detecting.

A further aspect of the invention relates to a method of determining whether a subject is at increased risk for cardiovascular disease. This method includes assessing the level of specific Apolipoproteins and/or lipoprotein particles present in a biological sample. The assessing includes the steps of providing a biological sample comprising lipoprotein particles and providing at least two lipoprotein-binding complexes. Each complex includes an antibody that binds a lipoprotein particle or a portion thereof, where the antibody is bound to a signal producing molecule capable of producing or causing production of a detectable signal. Each detectable signal of the at least two lipoprotein-binding complexes is distinguishable from the other detectable signal. The assessing step also includes separating the lipoprotein particles present in the biological sample by depositing the biological sample on an electrophoretic gel and carrying out gel electrophoresis; contacting the biological sample with the at least two lipoprotein-binding complexes under conditions suitable to form a lipoprotein-antibody-signal producing molecule complex; washing the gel to eliminate, or substantially eliminate, unbound antibody; detecting the detectable signal produced by the signal producing molecule of the lipoprotein-antibody-signal producing molecule complex on the electrophoretic gel; and determining the level of the specific Apolipoprotein and/or lipoprotein particle present in the biological sample based on the detecting. The method also includes the step of correlating the determined level of the Apolipoprotein and/or lipoprotein particle to a control or reference value to determine if the subject is at an increased risk for cardiovascular disease.

The assessing may include separating lipoprotein particles present in the biological sample by depositing the biological sample on an electrophoretic gel and carrying out gel electrophoresis; forming two or more lipoprotein-antibody-signal producing molecule complexes, where the two or more antibodies are specific to two or more different lipoprotein particles or a portion thereof; detecting the detectable signal produced by the signal producing molecules of the respective lipoprotein-antibody-signal producing molecule complexes on the electrophoretic gel; and determining the levels of the different Apolipoproteins and/or lipoprotein particles present in the biological sample based on the detecting.

Correlation in the context of lipid-related health risk, cardiovascular condition, and risk of cardiovascular disease, refers to a statistical correlation of the resulting lipoprotein size distribution with population mortality and risk factors, as well known in the art. Correlation in the context of monitoring cardiovascular risk (e.g., for responsiveness to a therapeutic intervention) refers to comparison of the lipoprotein size distribution at two time points (e.g., before and after a therapeutic intervention is conducted).

The correlating may include correlating the determined levels of the different Apolipoproteins and/or lipoprotein particles to a control or reference value to determine if the subject is at an increased risk for cardiovascular disease.

The correlating may also include assigning the subject to a risk category selected from the group consisting of high risk, intermediate risk, and low risk (or optimal) groups for developing or having cardiovascular disease. There are well established recommendations for cut-off values for biochemical markers (for example, and without limitation, cholesterol and lipoprotein levels) for determining risk (see BRAUNWALD'S HEART DISEASE: A TEXTBOOK OF CARDIOVASCULAR MEDICINE 9th ed. (Bonow et al. eds. 2011); "Executive Summary of The Third Report of The National Cholesterol Education Program (NCEP) Expert Panel on Detection, Evaluation, And Treatment of High Blood Cholesterol In Adults (Adult Treatment Panel III)," *JAMA* 285:2486-2497 (2001); "Adult Treatment Panel III (ATP III) of the National Cholesterol Education Program. Implications of Recent Clinical Trials for the National Cholesterol Education Program Adult Treatment Panel III Guidelines," Circulation 110(2):227-39 (2004); and MedlinePlus, A service of the U.S. National Library of Medicine and National Institutes of Health available at nlm.nih.gov/medlineplus, each of which is hereby incorporated by reference in its entirety.) For instance, anti-ApoB binding/detection may be correlated to cut-off estimates for assigning a risk category based on Lp(a)-P and LDL-P. For instance, the cut-off values for assigning such risk categories may be as follows: Lp(a)-P: <75 nmol/L optimal, 76-125 nmol/L intermediate risk, >126 nmol/L high risk; LDL-P: <1000 nmol/L optimal, 1000-1299 nmol/L intermediate risk, >1300 nmol/L high risk.

The above two or more different lipoprotein particles or portions thereof may comprise at least Apolipoprotein B and low density lipoprotein. An elevated level of Apolipoprotein B and low density lipoprotein particles detected indicates that an individual has increased risk for cardiovascular disease. Since there is a 1:1 stoichiometry between ApoB and VLDL, an elevated ApoB is arithmetically related to VLDL-P.

The different lipoprotein particles or portions thereof may include at least Apolipoprotein B and lipoprotein (a). An elevated level of lipoprotein (a) particles indicates that an individual has increased risk for cardiovascular disease.

The different lipoprotein particles or portions thereof may include at least Apolipoprotein B and Apolipoprotein C-III. The different lipoprotein particles or portions thereof may include at least Apolipoprotein B, Apolipoprotein C-III, Apolipoprotein E, or combinations thereof.

The invention also includes the ability to identify heretofore unknown lipid particle subclass ratios and levels of relevance, due to the difficulty of distinction, measurement and comparison. All other lipid particle measurement methods to date have relied on the isolation of a specific type of lipoprotein particle or apolipoprotein. The apolipoprotein is also usually isolated from its associated lipid particle by reducing/denaturating reagents. In these previous methods, multiple assays would be required to include a control and all distinct particles or apolipoproteins. For example, the previous non-specific lipoprotein immunofixation electrophoretic method only allows investigation of a single type of protein per assay, or lane in a gel, such as ApoB or Apo A-I, but not both. In the specific cocktailed lipoprotein immunofixation electrophoresis assay, a single lane will contain all of the necessary components for evaluating ratios of distinct lipid particles or apolipoproteins.

The invention also includes a method for rapidly identifying clinically-relevant lipid particle associated apolipoprotein(s), and combined ratios. A reagent solution combining multiple labeled antibodies targeting various antigens may be applied to each biosample separation in a clinically-relevant sample population. Using methods described herein, multiple ratios of labeled particles can be calculated and correlated to patient health outcomes. Ratios that correlate to specific health outcomes may be determined. The ratios may be presented for clinical actions comprising diagnostic assessment, risk assessment, or selecting a therapy regimen based on the risk of cardiovascular disease determined.

The invention also includes selecting a therapy regimen based on the risk for cardiovascular disease determined. For instance, an individual may be determined to be at an elevated risk according to the methods and a treatment regimen may then be selected based on the elevated risk.

The selected therapy regimen may include drugs or supplements. Suitable drugs or supplements include those administered for the purpose of lowering serum cholesterol, lowering LDL, IDL, and VLDL, Lp(a) and/or raising HDL, as known in the art.

Examples of suitable drugs include an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, an angiotensin system inhibitor, or combinations thereof.

The selected therapy regimen may also involve giving recommendations on making or maintaining lifestyle choices based on the risk for cardiovascular disease determined. Lifestyle choices may involve changes in diet, changes in exercise, reducing or eliminating smoking, or a combination thereof.

A report may also be generated that includes, among other things, a description of the selected treatment regimen. In some embodiments, the results of lipoprotein analyses are reported in such a report. A report refers in the context of lipoprotein and other lipid analyses to a report provided, for example to a patient, a clinician, other health care provider, epidemiologist, and the like, which includes the results of analysis of a biological specimen, for example a plasma specimen, from an individual. Reports can be presented in printed or electronic form, or in any form convenient for analysis, review and/or archiving of the data therein, as known in the art. A report may include identifying information about the individual subject of the report, including without limitation name, address, gender, identification information (e.g., social security number, insurance numbers), and the like. A report may include biochemical characterization of the lipids in the sample, for example without limitation triglycerides, total cholesterol, LDL cholesterol, and/or HDL cholesterol, and the like. A report may further include characterization of lipoproteins, and reference ranges therefore, conducted on samples prepared by the methods provided herein. The term "reference range" and like terms refer to concentrations of components of biological samples known in the art to reflect typical normal observed ranges in a population of individuals. Exemplary characterization of lipoproteins in an analysis report may include the concentration and reference range for VLDL, IDL, Lp(a), LDL and HDL, and subclasses thereof. A report may further include lipoprotein size distribution trends.

The invention also may further include administering the selected treatment regimen to the subject. Accordingly, a further aspect of the present invention relates to a method of treating a subject having an elevated risk for cardiovascular disease determined.

The invention also relates to a method of monitoring the risk for developing cardiovascular disease. This method includes determining whether a subject is at increased risk for cardiovascular disease at a first time point and repeating the determining at one or more later time points (e.g., before and after therapeutic intervention or at progressive time points during a course of therapeutic intervention). The determined risk at each progressive time point is compared the determined risk from one or more earlier time points to evaluate whether the subject's risk for developing cardiovascular disease has increased or decreased, thereby monitoring the risk for developing cardiovascular disease. This method may involve assigning a risk category based on the determined risk for developing cardiovascular disease and comparing the risk categories assigned at progressive time points (e.g., comparing a first risk category determined at a first time point to a second risk category taken at a second time point), thereby monitoring the risk for developing cardiovascular disease.

As noted above, the prior electrophoretic technology required transfer protocols or traditional IFE non-protein specific staining of crosslinked probed complex. Further, existing strategies to measure detect and quantify lipid protein particles use non-specific protein dye to detect the fixed proteins in a gel (U.S. Patent Application Publication No. 2012/0052594, which is hereby incorporated by reference in its entirety). This invention provides more efficient systems and methods to detect and quantify apolipoproteins and lipoproteins particles that avoid the use of transfer-blot technology.

An example of a laboratory method of non-specific Lipo-IFE method includes: 1) obtaining a biosample, 2) preparing the biosample to just include serum, 3) applying the biosample to the gel, 4) separating lipid particles by electrophoresis, 5) applying polyclonal antibodies to the gel to fix ApoB, 6) washing the gel to get rid of anything that is not a lipidparticle bound to an Antibody-ApoB complex, 7) staining the gel with a non-specific protein stain, 11) repeating the process in parallel for various immunologically-active targets such as Apo A-I, Apo A-II, Apo E2, Apo E3, and Apo E4 in independent lanes. FIG. 1 shows a representation of a final non-specific lipoprotein immunofixation electrophoresis gel for the identification of various lipoprotein particles. Before the immunofixation procedure, biosamples (in this case serum samples) are prepared as needed to separate the intact lipid particles by gel electrophoresis. Each lane, in the figure labeled as columns ApoB, Apo A-I and Apo A-II, receives portions of the same patient serum sample. Native (not denatured or otherwise modified) components of the sample are separated by electrophoresis. Their separation is effected according to Charge and size.

For each lane, an antisera targeting a distinct apolipoprotein on a lipoprotein particle is applied to the gel fixing the lipoprotein/Lipid Particle complex in place in the lane and any associating additional protein with the particle. The gel is washed to remove non-immunofixed materials and a non-specific protein stain is applied to the gel. Subsequent analysis can be done to report relative amounts of lipoproteins in a lane, all of which are associated with the same apolipoprotein. The process is repeated in additional lanes with antisera to different apolipoproteins but using the same non-specific protein stain. Immunofixation and staining are carried out on the same gel as the electrophoresis procedure.

Antisera is composed of monoclonal or polyclonal antibodies targeted at a specific apolipoprotein as it exists on the surface of a lipoprotein particle. Because subsequent analysis is non-specific, the antisera can only be directed to a single antigen. Analysis is limited to relative levels of particles having the same apolipoprotein attached to the protein. An example of a method of analysis of a non-specific Lipo-IFE includes: 1) differentiating the detected bands in a gel lane by manually or automatically determining boundaries around each band, 2) associating each band with distinct ApoB-bound lipidparticles, 3) assigning the bands to different particles, 4) obtaining a total concentration number for ApoB-bound lipid particles from a different assay such as ultracentrifugation or NMR, 5) calculating the particle numbers based on optical density and position in the gel and absolute particle number, 6) assessing patient risk level for cardiovascular disease, diabetes mellitus, or any other condition by absolute reported particle level, and/or 7) calculating a ratio of particles levels with clinical significance and assessing patient risk level for cardiovascular disease, diabetes mellitus, or any other condition by particle level ratios, and 8) reporting said risk level.

On the other hand, an example of a method of the invention using specific Lipo-IFE includes: 1) obtaining a biosample, 2) preparing the biosample to just include serum, 3) applying the biosample to the gel, 4) separating lipid-proteins by electrophoresis, 5) applying fluorescently-tagged polyclonal antibodies to the gel to bind to a multiplicity of apolipoprotein moieties on lipoparticles in the gel lane, 6) washing the gel to get rid of anything that is not a lipoparticle-antibody complex 7) detecting all lipoparticles associated with a different fluorescent tag in different bands on the gel 9) assigning distinct fluorescent signals to different apolipoproteins on lipid particles 10) obtaining a total concentration number for lipid particles from a different assay such as ultracentrifugation or NMR, 11) calculating the particle numbers based on some combination of optical density/emission coefficients, fluorescent signal wavelength, position in the gel and absolute particle number. Further, in a diagnostic method, one may calculate a ratio of apoparticles detected in the previous example such as ApoB/ApoAI, and assess risk for CHD based on the calculated ratio.

Figure 2:
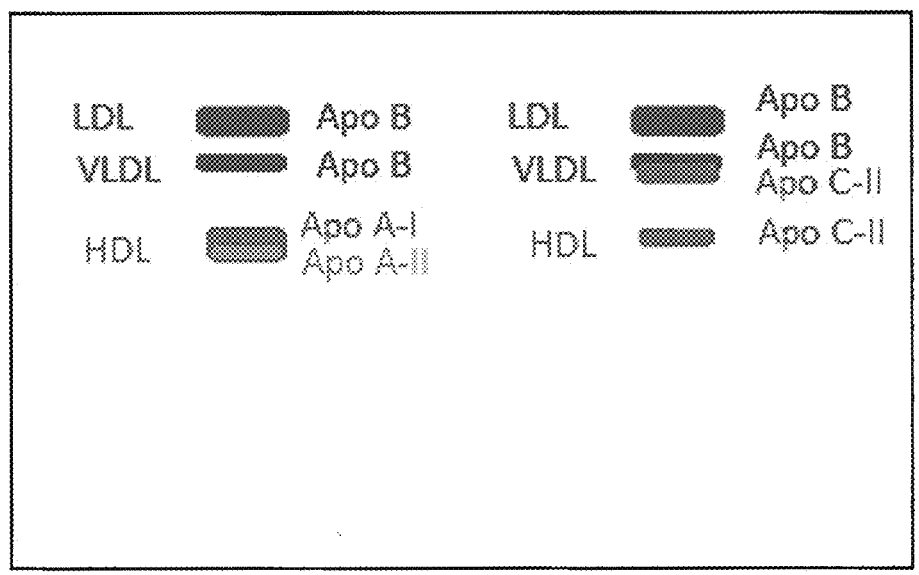
FIG. 2 is a schematic illustration of a gel after specific, cocktailed Lipo-IFE.

FIG. 2 is a representation of an exemplary final specific lipoprotein immunofixation electrophoresis gel, applied with cocktailed, individually-labeled antibodies. Before the immunofixation procedure, biosamples (in this case serum samples) are prepared as needed to separate the intact lipid particles by gel electrophoresis. Either identical aliquots of a single patient sample are applied to different lanes in the gel, or different patient samples are applied to each gel lane. FIG. 2 is a representation of identical aliquots of a single patient sample to achieve different analysis. Separation is effected by zonal gel electrophoresis according to charge and size.

As described above, various cocktails of multiplexed antisera are made to be applied to a lane. For example, antisera in lane 1 comprises anti-ApoB antibodies labeled with a red fluorescent tag, anti-Apo A-I antibodies labeled with a green fluorescent tag, and anti-Apo A-II antibodies labeled with an orange fluorescent tag. Antibodies may by polyclonal or monoclonal. Immunofixation and staining are carried out on the same gel as the electrophoresis procedure. After application of the antisera to a lane, the gel may be blotted to remove excess antisera, washed to remove excess tagged antibodies and coincident non-immunofixed materials, blotted again, and dried. The gel is applied to a detection system, in this example a fluorescence detection system, to generate a visualization of the final gel for a user and analyze the quantities of each particle by label number and type.

Analysis instruments may include Biorad ChemiDoc MP and Syngene G:BOX F3. The analysis instrument may detect the narrow wavelength of a fluorescent tag on each antibody to distinguish overlapping bands.

Different colors may appear in the approximate or exact band in a gel lane, because some lipid particles contain more than one apolipoprotein, to which distinct antibodies are targeted, although their separation characteristics like particle charge and size are similar. In this example, a detection system will separately detect the fluorescent wavelength through a variety of possible means including narrow bandwidth detection and/or distinct excitation wavelengths.

The detection system can also adjust the output signal to be normalized with other signals output from the same lane by such variables as extinction/emission coefficients and transmissive strength, to accurately report relative and absolute concentrations of the separated lipoparticles and apolipoproteins.

EXAMPLES

The following examples are provided to illustrate embodiments of the present invention but are by no means intended to limit its scope.

Example 1

In Situ Detection of Apo-B and Apo-CIII

Figures 3A, 3B, 3C:
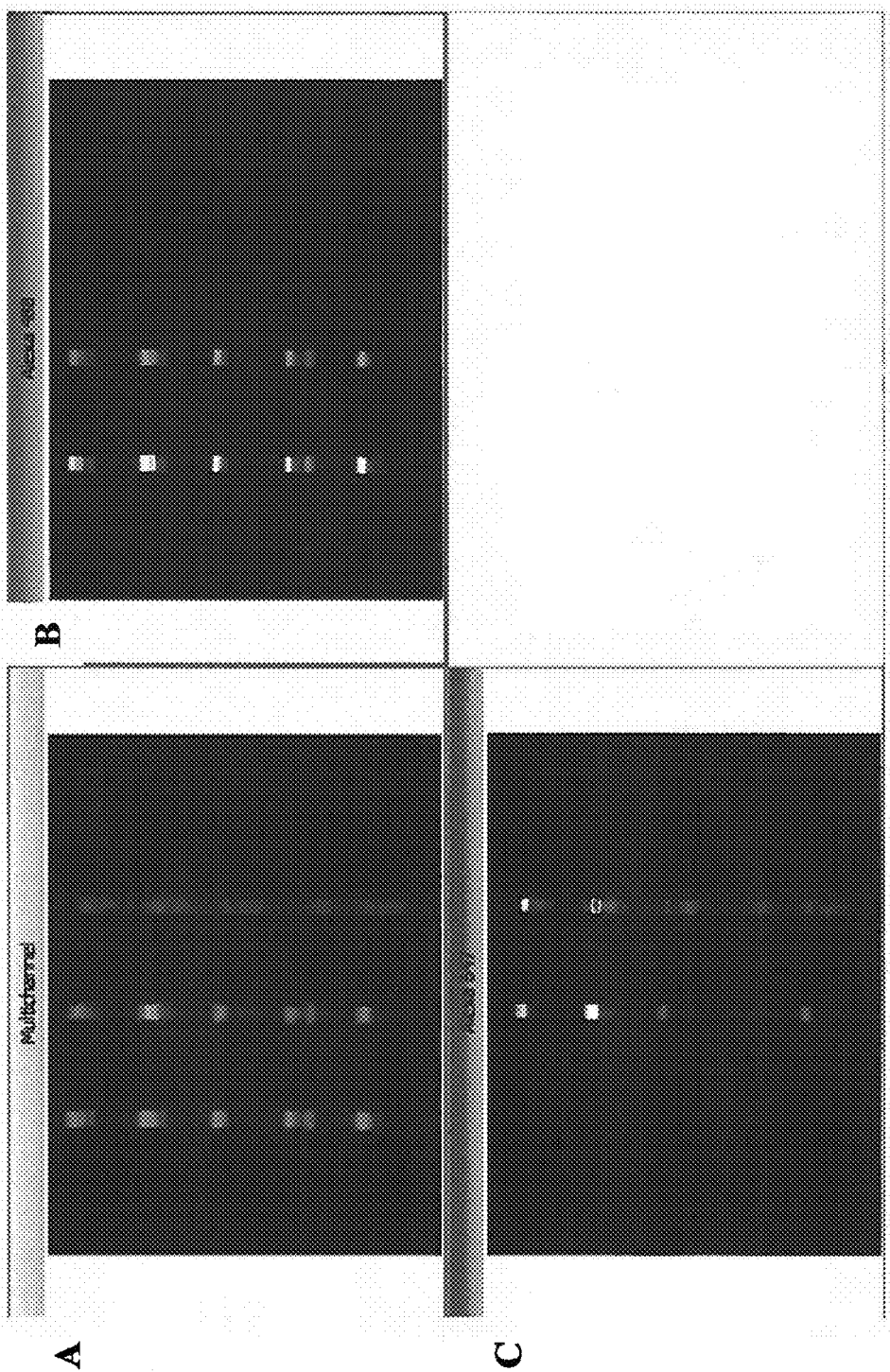
FIGS. 3A-3C are three images of a single agarose gel exhibiting the integrated detection technique with multiple antibody cocktail applied to an electrophoresed gel of multiple patient samples. Briefly, five patient samples were applied to a prepared gel in triplicate. The five samples are distributed vertically and the column application was repeated three times. Alexa 488 dyes (green emissions) were used to identify Apo-B-linked particles and Alexa 647 dyes (orange emissions) were used to identify Apo-CIII-linked particles.
Figures 4A, 4B, 4C, 4D:
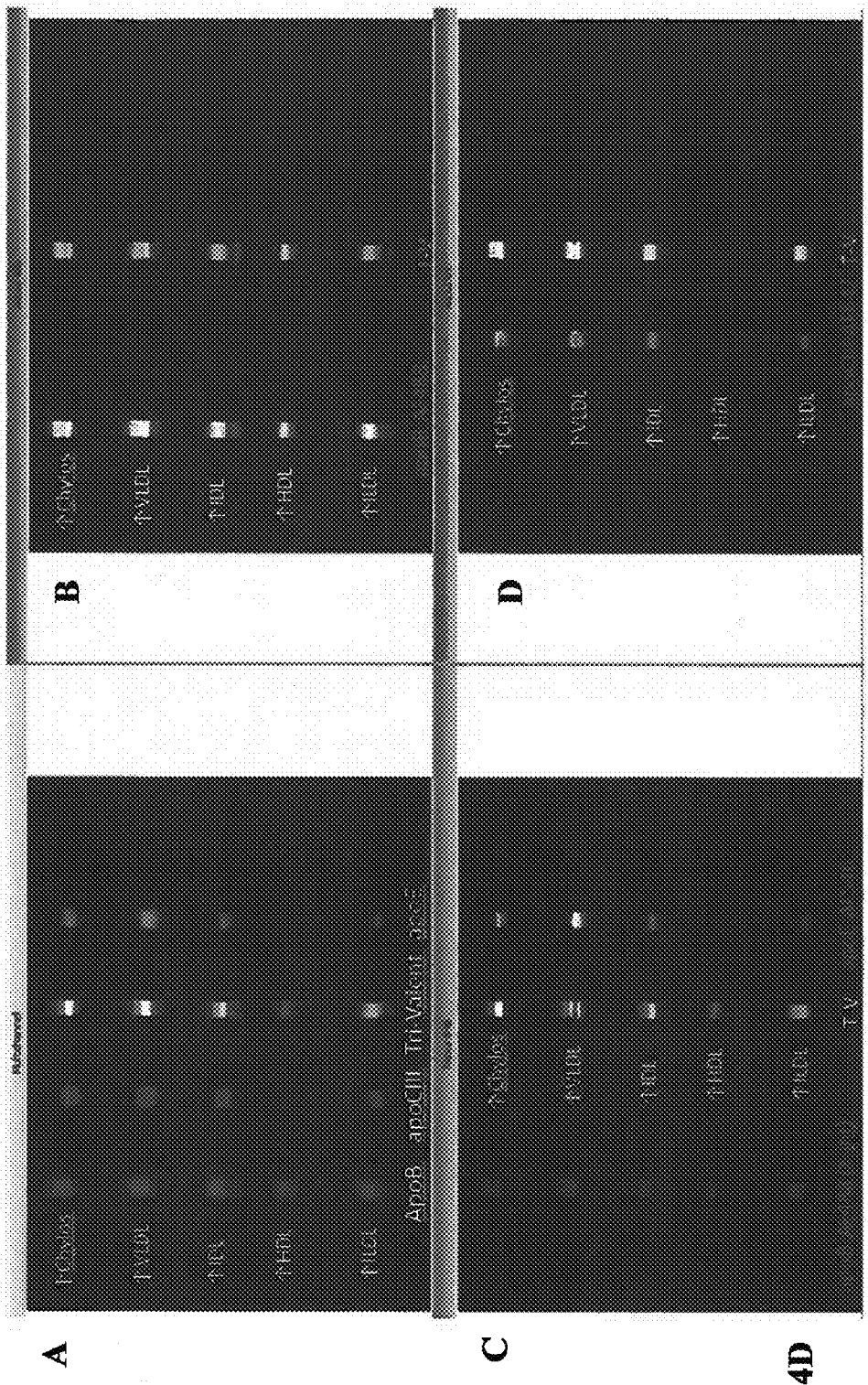
FIGS. 4A-4D are four images of a single agarose gel exhibiting the integrated detection technique with a trivalent antibody cocktail applied to an electrophoresed gel of multiple patient samples. Briefly, five patient samples were applied to a prepared gel in triplicate. The five samples are distributed vertically and the column application was repeated four times. Alexa 488 dyes (blue emissions) were used to identify Apo-B-linked particles, Alexa 647 dyes (orange emissions) were used to identify Apo-CIII-linked particles, and Alexa 546 dyes (green emissions) were used to identify Apo-E-linked particles.

FIGS. 3A-3C show an example of the integrated detection technique with multiple antibody cocktail applied to an electrophoresed gel of multiple patient samples. In particular, five patient samples were applied to a prepared gel in triplicate. The five samples are distributed vertically and the column application was repeated three times. Alexa 488 dyes (green emissions) were used to identify Apo-B-linked particles and Alexa 647 dyes (orange emissions) were used to identify Apo-CIII-linked particles. The materials and methods employed are described in more detail below.

The patient samples underwent electrophoreses, separating the lipoproteins in each lane as described in U.S. Patent Application Publication No. 2012/0052594, which is hereby incorporated by reference in its entirety. DI water was substituted for the TBS wash/re-hydration of the gel post electrophoresis and an immunofixation. In general, a SPIFE Electrophoresis System by Helena Laboratories Corporation was used to analyze serum samples from various patients. Patient samples were pipetted into sample cups in an array corresponding to the lanes in the gel. An applicator assembly contacted the patient samples to adsorb sample and transfer to the surface of the agarose gel. Electrodes were connected to opposite ends on the gel blocks and voltage applied to instigate electrophoretic migration.

The electrodes were removed following electrophoresis and the gel blocks were removed and discarded. Apo-B antiserum conjugated to Alexa 488 fluorescent dye was applied to lane 1. Apo-CIII antiserum was conjugated to Alex 647 fluorescent dye was applied to lane 3. A combination of Apo-B and Apo-CIII antiserum was applied to lane 2. Excess antiserum was washed from the gel and the gel was dried.

The dried gel was analyzed in a Bio-Rad Chemidoc MP Imaging System with sequential excitation and imaging of Alexa 488 and Alexa 647 dyes. Images of the gel are shown in FIGS. 3A-3C. The bottom left (FIG. 3C) is a raw image of the Alexa 647 emission and the upper right (FIG. 3B) is a raw image of the Alexa 488 emission taken from the same gel at different wavelengths. The upper left image (FIG. 3A) is processed for the user to visualize the combination images in different colors. The subsequent images can be further analyzed for band intensity to quantify the lipoparticle concentrations.

As noted above, the panel on the bottom left (FIG. 3C) shows fluorescence from the Alexa 647 dyes conjugated to Apo-CIII antibodies. Apo-CIII is especially prevalent in VLDL and HDL particles, and shows up with greatest intensity in those bands in lanes 2 and 3.

As also noted above, the panel on the upper right (FIG. 3B) shows fluorescence from the Alexa 488 dyes conjugated to Apo-B antibodies. Apo-B is found in LDL, VLDL, and Lp(a) particles.

A computerized analysis can process the images in the upper right (FIG. 3B) and lower left (FIG. 3C) to quantify lipoparticle concentrations on a single gel. The upper left image (FIG. 3A) presents composite image result of both anti-apoB and anti-apoCIII IFE probes, i.e., an over-layed picture of color coded bivalent antibody probes for linked ApoB and linked APO-CIII in their respective lipid particles. The multiple antibody cocktail technique allows simultaneous and independent antibody quantification on the same sample on the same gel.

The samples chosen for analysis represent patients with independent elevations of VLDL and HDL in the presence of elevations of LDL and Lp(a)-P. The analysis of such samples demonstrates the ability of the methods described herein to discriminate relative apolipoprotein presence in respective lipid particles.

The top two samples demonstrate the ability of the methods described herein to determine probed apolipoproteins in elevated VLDL in the presence of LDL, Lp(a) with minimal HDL contribution. The bottom two samples demonstrate the ability of the methods described herein to determine probed apolipoproteins in elevated HDL in the presence of elevated Lp(a) with minimal VLDL contribution. The center sample demonstrates the ability of the methods described herein to determine probed apolipoproteins in modest elevations of LDL, VLDL and HDL.

As shown in FIGS. 3A-3C, the bottom three samples all indicate high levels of LDL (which is indicated by the detected presence of Apo-B) and HDL (which is indicated by the detected presence of Apo-CIII) without VLDL (which is indicated by lack of Apo-CIII near the LDL position). The third sample from the top shows high levels of Apo-B-linked LDL and Apo-CIII-linked HDL. The second sample from the bottom shows Apo-B-linked LDL and Lp(a). The bottom sample shows Apo-B-linked LDL, some Apo-CIII-linked HDL, and trace Apo-B-linked Lp(a).

Example 2

In Situ Detection of Apo-B, Apo-CIII, and ApoE

In a second experiment, monovalent and trivalent fluorescence antibody probes were prepared and successfully shown to probe apolipoproteins in intact lipid particles separated by electrophoresis on a single gel matrix. Patient samples with known lipoparticle profiles were prepared and applied to gels for separation and analysis according the same protocols as Example 1. The known lipoparticle compositions included those with increased chylomicron content, increased VLDL content, increased LDL content, two with increased IDL content, and increased HDL content. After separation, the lanes were probed with anti-ApoB conjugated to Alexa 488, anti-ApoC-III, conjugated to Alexa 647, and anti-ApoE conjugated to Alexa 546, independently (with monovalent probes) and collectively (the trivalent probes). The resultant labeled lipoprotein gels were exposed to fluorescence imaging and the peaks were recorded. The raw gel images are presented in FIGS. 4A-4D.

In this experiment, anti-ApoB conjugated to Alexa 488 reagents were optimized to be able to generate quantitative results. Anti-ApoCIII (conjugated to Alexa 647) and anti-ApoE (conjugated to Alexa 546) were not optimized and show qualitative results only, so only indications of lipoparticle presence are concluded with said probes.

Fluorescence scanner imaging using a Bio-Rad ChemiDoc MP permits relative quantitative analysis of the electrophoretically separated intact lipid particle apolipoproteins by (a) importing a total apolipoprotein concentration with relative Area-Under-Curve analysis to enable "tandem" molar apolipoprotein concentrations or (b) internal (in-situ) calibrators, with relative Area-Under-Curve analysis will enable on-gel independent molar apolipoprotein concentrations. Either method is routinely practiced by those skilled in the art.

Figures 5A, 5B, 5C:
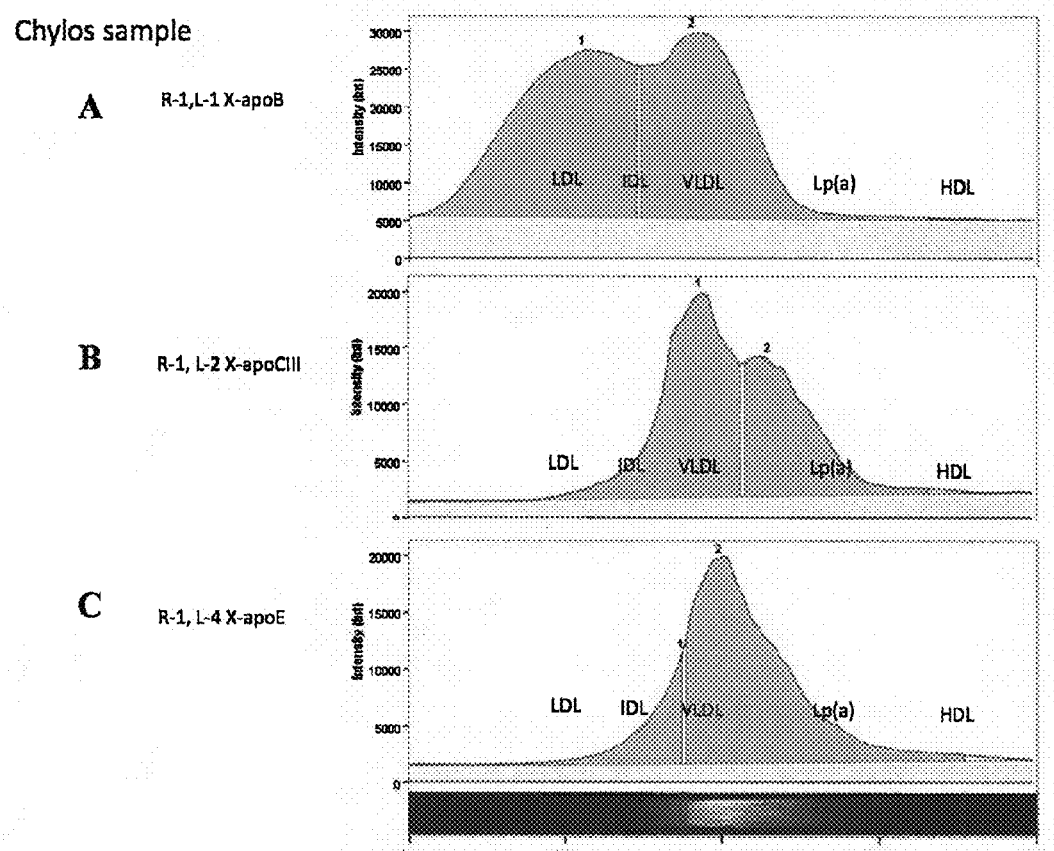
FIGS. 5A-5C are density scans of row 1 of the gel in FIGS. 4A-4D for a sample with increased chylomicron content. Chylomicrons have been shown to contain ApoB, ApoCIII, and ApoE, and they are electrically neutral in the alkaline gel used in this experiment, generally showing up on the gel between IDL and VLDL.

The presented system show separation of five lipoprotein particle classes by electrophoresis and each probed with three specific antibodies to produce fifteen simultaneous analyses on a single serum sample. Five sample scans were performed on the gel in FIGS. 4A-4D and densitometry scans are shown in FIGS. 5 through 10, as follows:

FIGS. 5A-5C: Sample 1, serum with elevated Chylomicrons. Chylomicrons are electrically neutral in this protocol and unlabeled in the figure because of increased variance over non-neutral particles. Analysis by electrophoretic gel may be supported by visually observed turbidity and comparisons between plasma samples before and after chylomicrons are removed by centrifugation. ApoE is widely understood to be a part of Chylomicrons, but evidence indicates the concentration is less than other particles types such as VLDL.

Figures 6A, 6B, 6C:
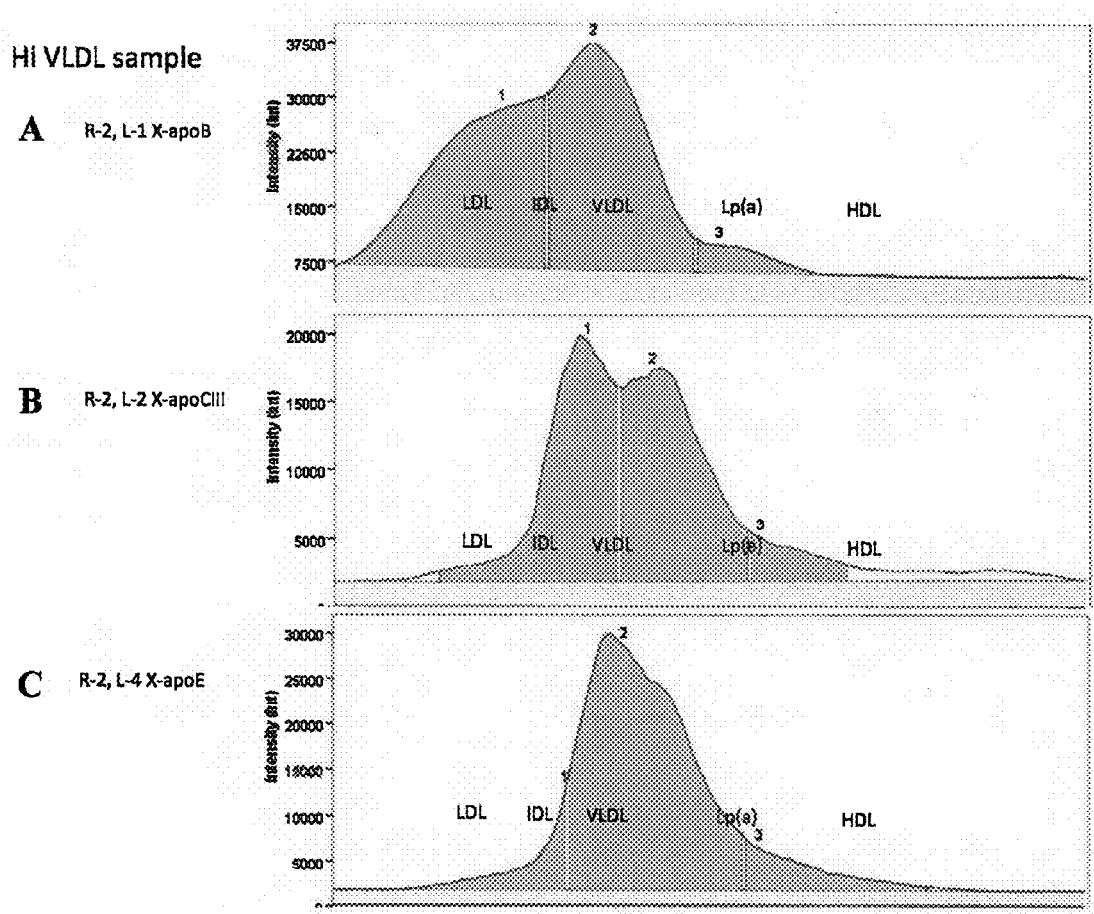
FIGS. 6A-6C are density scans of row 2 of the gel in FIGS. 4A-4D for a sample with increased VLDL content. VLDLs are known to contain ApoB, ApoCIII, and ApoE.

FIGS. 6A-6C: Sample 2, serum with elevated VLDL-P. VLDL contains Apo-B, Apo-CIII, and Apo-E, thus results showing evidence of all three probes in the figures.

Figure 7A:
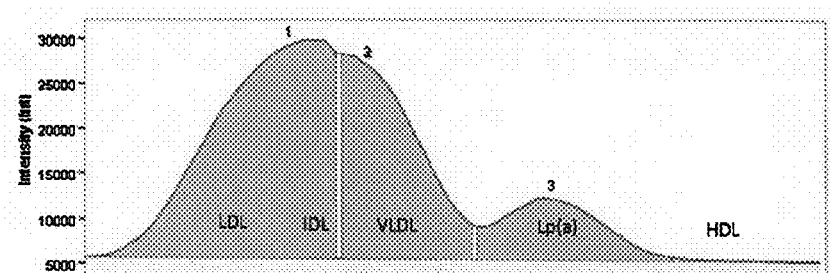
FIGS. 7A-7C are density scans of row 3 of the gel in FIGS. 4A-4D for a sample with increased IDL content. IDLs are known to contain ApoB, ApoCIII, and ApoE.
Figure 7B:
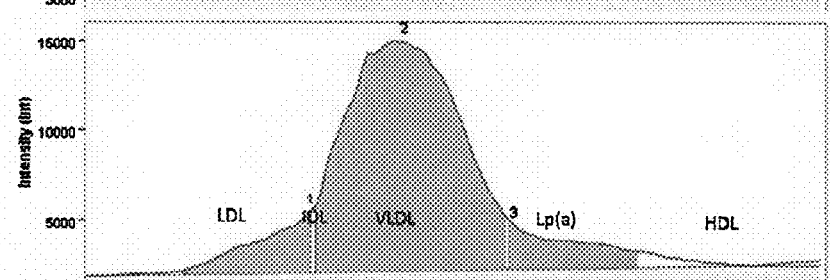
Figure 7C:
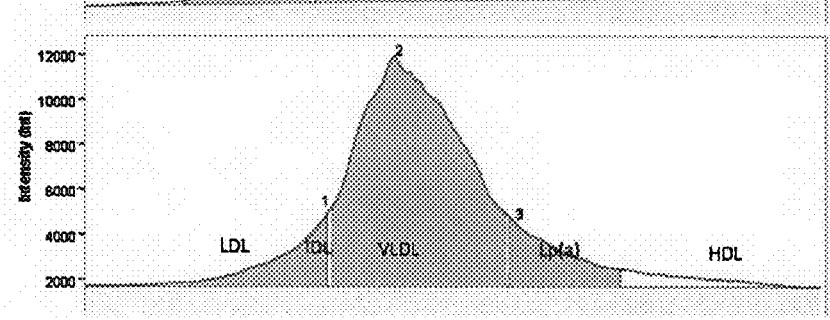

FIGS. 7A-7C: Sample 3, serum with elevated IDL-P. There is evidence of IDL Apo-B content at higher concentrations than either Apo-CIII or Apo-E, despite the presence of all three apolipoproteins in IDL. The Apo-B peak is larger than its counterparts, and Apo-CIII and Apo-E peaks are present but in lower levels than VLDL particle composition.

Figures 8A, 8B, 8C:
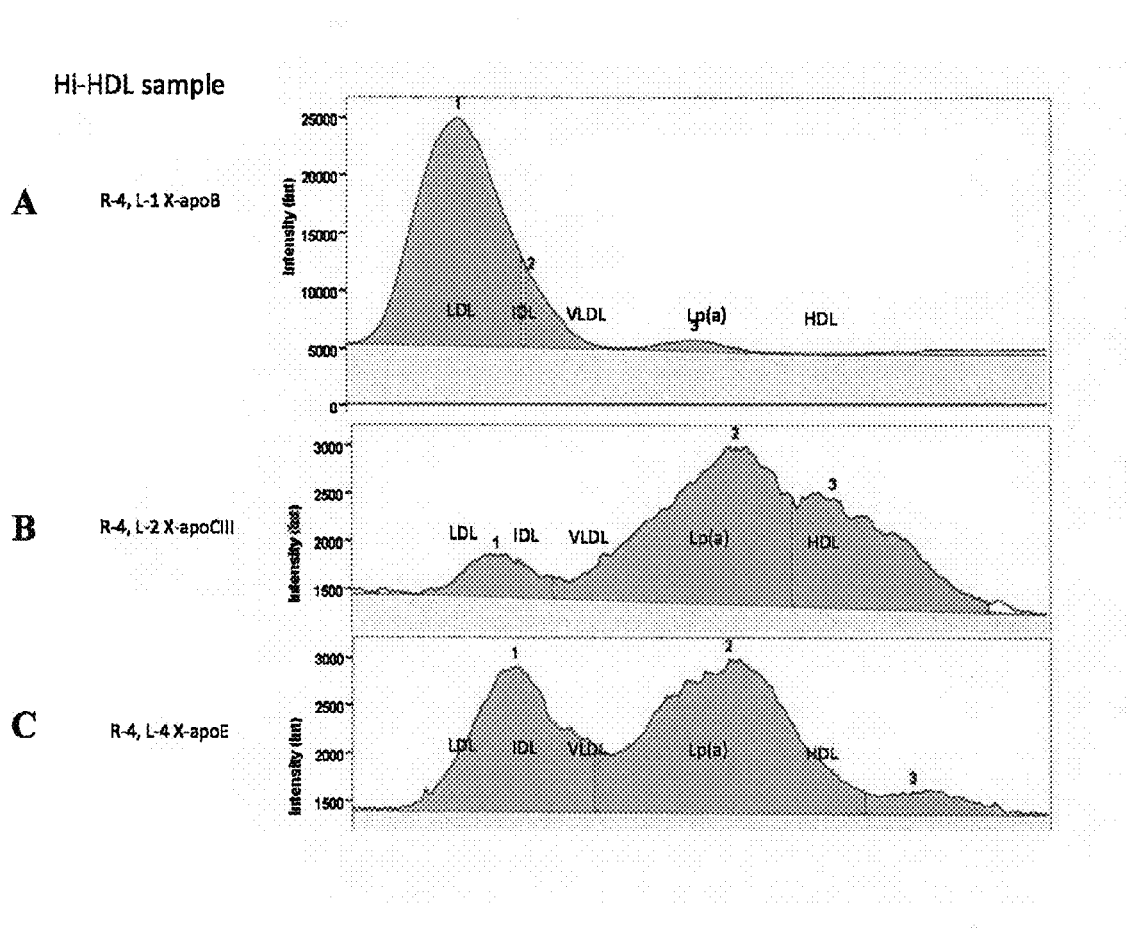
FIGS. 8A-8C are density scans of row 4 of the gel in FIGS. 4A-4D for a sample with increased HDL content. HDLs are known to contain ApoCIII, and ApoE.

FIGS. 8A-8C: Sample 4, serum with elevated HDL-P. The specificity of the tagged antibodies confirms the qualitative presence of the targeted apolipoproteins in their respective lipid particles. Although the apoB probe yielded expected results, the provocative presence of apoCIII and apoE in the Lp(a) region requires further investigation. The unprecedented nature of this technology provides heretofore unavailable insight into equilibrium dynamics of lipid particle composition. The unprecedented specificity of analysis of lipoprotein content by protein content shows expected results for HDL-P apo-B content (none is expected), and unexpected apo-CIII and apo-E content near the Lp(a) position.

Figure 9A:
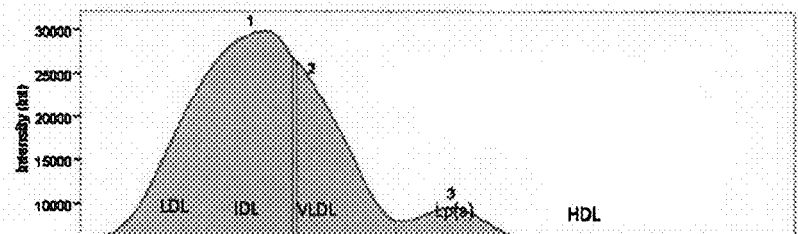
FIGS. 9A-9C are density scans of row 5 of the gel in FIGS. 4A-4D for a sample with increased IDL content. IDLs are known to contain ApoB, ApoCIII, and ApoE.
Figure 9B:
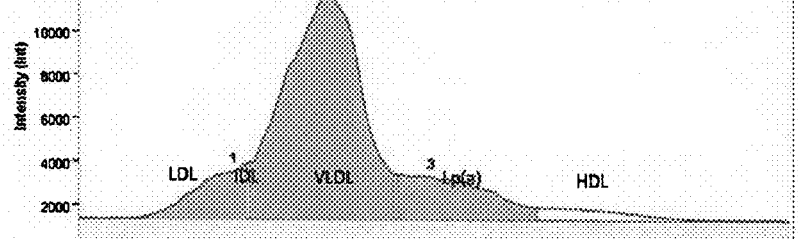
Figure 9C:
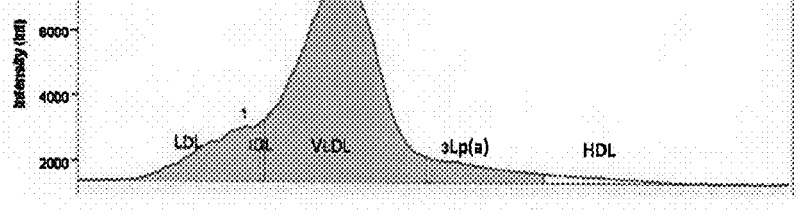

FIGS. 9A-9C: Sample 5, a second serum with elevated IDL-P. Results for apo-B and apo-CIII are expected, showing high apo-B content corresponding to the elevated IDL particles and evident apo-CIII content, proportionally less than the VLDL content. Apo-E content is evident in the IDL particles in 9C, with unexpected peaks near the VLDL positions.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of assessing a level of specific lipoprotein particles present in a biological sample comprising:
providing a biological sample comprising lipoprotein particles;
providing a first and a second lipoprotein-binding complex, wherein the first lipoprotein binding complex comprises an antibody that binds to a first lipoprotein particle or portion thereof wherein the antibody is bound to a first signal producing molecule capable of producing or causing production of a first detectable signal and the second lipoprotein-binding complex comprises a second antibody that binds to a second lipoprotein particle or portion thereof, wherein the second antibody is bound to a second signal producing molecule capable of producing or causing production of a second detectable signal and wherein the first and the second detectable signals are distinguishable from each other when detected in a single lane of an electrophoretic gel;

separating the lipoprotein particles present in the biological sample by depositing the biological sample on an electrophoretic gel and carrying out gel electrophoresis;

probing the lipoprotein particles or portions thereof with the first and second lipoprotein-binding complexes to produce the first and the second detectable signals;

detecting the first and the second detectable signals on the electrophoretic gel; and determining the level of the first and the second lipoprotein particles or portions thereof present in the biological sample based on said detecting.

2. The method of claim 1, wherein the first and second lipoprotein particles or portion thereof are independently selected from the group consisting of Apolipoprotein A, Apolipoprotein B, Apolipoprotein C, Apolipoprotein D, Apolipoprotein E, Apolipoprotein H, lipoprotein (a), high density lipoprotein, intermediate density lipoprotein, low density lipoprotein, very low density lipoprotein, Chylomicrons, Lipoprotein X, oxidized variants and mixtures thereof.

3. The method according to claim 2, wherein the first lipoprotein particle or portion thereof comprises Apolipoprotein B.

4. The method according to claim 2, wherein the second lipoprotein particle or portion thereof comprises oxidized low density lipoprotein.

5. The method according to claim 1, wherein said determining step comprises: quantitating the level of lipoprotein particles based on said detecting.

6. The method according to claim 5 further comprising: determining relative ratio(s) of lipoprotein particles present in the biological sample based on said quantitating.

7. The method according to claim 1, wherein the detectable signal is detectable by fluorometric means.

8. The method of claim 1, wherein the first and second lipoprotein particles or portions thereof are independently selected from the group consisting of Apolipoprotein A, Apolipoprotein B, Apolipoprotein C, Apolipoprotein D, Apolipoprotein E, Apolipoprotein H, lipoprotein (a), high density lipoprotein, intermediate density lipoprotein, low density lipoprotein, very low density lipoprotein, Chylomicrons, Lipoprotein X, oxidized variants and mixtures thereof.

9. The method of claim 8 wherein the apolipoprotein A comprises apolipoprotein A-I, apolipoprotein A-II or apolipoprotein A-IV.

10. The method of claim 8 wherein the apolipoprotein B comprises apolipoprotein B48 or apolipoprotein B100.

11. The method of claim 8 wherein the apolipoprotein C comprises apolipoprotein C-1, apolipoprotein C-II, apolipoprotein C-III or apolipoprotein C-IV.

12. The method of claim 8 wherein the apolipoprotein E comprises apolipoprotein E-2, apolipoprotein E-3 or apolipoprotein E-4.

* * * * *